United States Patent [19]
Rydell et al.

[11] Patent Number: 5,445,638
[45] Date of Patent: Aug. 29, 1995

[54] BIPOLAR COAGULATION AND CUTTING FORCEPS

[75] Inventors: Mark A. Rydell, Golden Valley; Joseph A. O'Brien, Fridley, both of Minn.

[73] Assignee: Everest Medical Corporation, Minneapolis, Minn.

[21] Appl. No.: 92,558

[22] Filed: Jul. 16, 1993

Related U.S. Application Data

[63] Continuation-in-part of Ser. No. 28,897, Mar. 8, 1993, abandoned.

[51] Int. Cl.[6] .............................. A61B 17/39
[52] U.S. Cl. ..................... 606/51; 606/171
[58] Field of Search ............ 606/45, 46, 48–52, 606/171

[56] References Cited

U.S. PATENT DOCUMENTS

| | | | |
|---|---|---|---|
| 4,655,216 | 4/1987 | Tischer | 606/51 |
| 5,190,541 | 3/1993 | Abele et al. | 606/50 |
| 5,258,006 | 11/1993 | Rydell et al. | 606/52 |
| 5,267,998 | 12/1993 | Hagen | 606/50 |

OTHER PUBLICATIONS

"Two New Laparoscopic Instruments: Bipolar Sterilizing Forceps and Uterine Manipulator" by Stephen Corson, Medical Instrumentation, vol. 11, No. 1.

Cameron-Miller product brochure for Model 80-7527.

*Primary Examiner*—Lee S. Cohen
*Attorney, Agent, or Firm*—Haugen and Nikolai

[57] ABSTRACT

A bipolar electrosurgical device for coagulating and cutting tissue has an elongated tubular member from which a bipolar tissue cutting forceps and cutting instrument extends at the distal end. The cutting instrument is connected to a moveable rod extending through the lumen of the tubular member. A first and second conductor pair extend in spaced apart parallel arrangement to allow the cutting instrument and its moveable rod to extend therebetween. The first and second conductor pairs are operatively connected to the forceps jaws. A moveable guide member is disposed within the lumen of the elongated tubular member and has means for selectively engaging the first and second conductor pairs for closing and opening jaws of the forceps. The forceps jaws have a slot for receiving the cutting instrument therebetween. A handle member is fixed to the proximal end of the first tubular member. The handle member includes means for imparting translational longitudinal reciprocal motion to the guide member and the cutting instrument for a coagulating and cutting procedure. The cutting instrument may have one cutting edge on the leading edge or a cutting edge on both the leading and trailing edge.

23 Claims, 6 Drawing Sheets

Fig.-7C

BIPOLAR COAGULATION AND CUTTING FORCEPS

This application is a continuation-in-part of application Ser. No. 08/028,897, filed Mar. 8, 1993, and entitled "BIPOLAR COAGULATION AND CUTTING FORCEPS", now abandoned.

BACKGROUND OF THE INVENTION

I. Field of the Invention

The present invention relates generally to electrosurgical instruments, and more particularly to a bipolar electrosurgical device for coagulation and cutting of target tissue and specifically designed for use in the performance of percutaneous laparoscopic surgery such as laparoscopic cholecystectomy, or similar endoscopic procedures.

II. Background of the Invention

For a number of years, the medical device industry, in cooperation with health care providers, has been developing methods and devices to permit surgical procedures to be performed in a less invasive manner. Minimally invasive surgery (MIS) generally involves the use of instruments which avoid the need to make major incisions in the body. Such major incisions usually require a relatively long period of hospitalization and subsequent home recovery. Using laparoscopic procedures, gall bladder removal can now be performed routinely through a trocar cannula. Surgeons are also performing appendectomies and hysterectomies through a trocar cannula.

When these MIS procedures are performed laparoscopically, the cutting and coagulating instruments most often used are either electrosurgical or laser based. Although capable of more precise cutting than electrosurgical instruments, lasers are somewhat difficult to control, particularly in the closed conditions of laparoscopic procedure. Laser systems are also expensive to acquire and sometimes inconvenient for the physician due to the problems of scheduling the limited number of laser units which would tend to be available in a typical hospital and the high level of expertise required in operating the laser scalpel.

MIS procedures are typically performed using monopolar electrosurgical instruments, which have inherent characteristics that pose certain risks for patients. In electrosurgery, radio frequency (RF) energy is used both to cut and coagulate tissue. In monopolar devices, the RF energy must pass from the surgical area and the surgical instrument through the patient's body to separate electrodes attached to a large surface area, generally the buttocks or thigh. In monopolar electrosurgery, there is a greater potential for injury to body tissues as the electrical current passes through them to the surface or return electrode. Skin burns can also occur at the site of the return electrode. In laparoscopic procedures, there is even a greater potential for complications when using monopolar instruments, due to the combined effects of the surgeons limited field of vision, the proximity of other organs and the inherent tendency of surgical instruments to conduct monopolar RF energy.

Bipolar electrosurgical products provide an improved margin of patient safety in certain minimally invasive surgical and interventional procedures. In bipolar devices, the RF energy is contained at the surgical site because both the active and return electrodes are located on the surgical instrument itself.

As mentioned above, a common laparoscopic surgical procedure is a laparoscopic cholecystectomy. Laparoscopic surgery is performed through several openings in the body which are made using trocars inserted through very small punctures. In a first such puncture a rigid endoscope called a laparoscope is inserted through a trocar to give the surgeon a view of the operative area. An electrosurgical device is inserted through a different trocar to allow required cutting and coagulation. Other grasping instruments may also be used in manipulating the organ being excised as connective tissue is being cut.

OBJECTS OF THE INVENTION

The present invention is directed to a bipolar electrosurgical instrument which is specifically designed to be insertable through a cannula for use in dissection of tissue or organs from surrounding structures to which they attach and which may also be used for a coagulating, cauterizing and cutting, as the need arises, during the laparoscopic procedure. Thus, the more expensive laser surgical instrument can be dispensed with and replaced with a disposable, low-cost substitute.

It is a principle object of the present invention to provide an improved instrument for carrying out laparoscopic surgical procedures within the abdominal cavity.

Another object of the present invention is to provide an improved electrosurgical instrument for coagulating tissue to be cut and then subsequently cutting.

Yet another object of the present invention is to provide a bipolar electrosurgical forceps having a cutting blade which allows precise control of the location where cutting is intended than can be achieved with present electrosurgical instruments.

Still another object of the present invention is to provide a flexible cutting instrument which can overcome a tissue obstruction and still perform a cutting operation.

SUMMARY OF THE INVENTION

The foregoing features, objects and advantages of the present invention are attained by providing an electrosurgical forceps-type instrument comprising a generally rigid tube having a proximal end, a distal end and a lumen extending from the proximal end to the distal end. The outside diameter of the tube is sufficiently small to permit it to be passed through a cannula percutaneously positioned through the abdominal wall. The length of the rigid tube is sufficient to permit bipolar coagulating forceps and a cutting instrument located at the distal end thereof to reach the internal organ to be surgically treated when the instrument is inserted through the cannula.

The bipolar coagulating forceps are connected by insulated conductive wires extending through the length of the tube to a source of RF power and to a means for opening and closing the forceps jaws. A cutting instrument located at the distal end of the rigid tube is connected to a device at the proximal end for providing longitudinal movement of the blade. The cutting instrument can take on various forms. The first embodiment is a scalpel blade with a cutting edge on its proximal end. The second embodiment is a sharpened springy wire in the shape of an L. It has a sharpened cutting edge on the leading and trailing edges of the downwardly depending leg. A third embodiment is a scalpel blade with an angled portion at its distal end.

The angled portion has a sharpened cutting leading and trailing edge. The last two embodiments are advantageous if the leading cutting edge meets too much of an obstruction, the cutting instrument can flex and ride up over the obstruction so that when the blade is pulled back, cutting can also take place on the return stroke.

The bipolar coagulating forceps comprise a pair of conductive jaws that can be opened and closed relative to one another for grasping tissue. Each jaw comprises an electrode surface for use in a coagulation operation and has a cutting blade receiving slot formed through its thickness dimension. The jaws project outwardly from the distal end of the rigid tube in spaced parallel arrangement with the slots aligned so that the cutting blade can move in a longitudinal reciprocal fashion in the slots to sever tissue pinched between the closed jaws. A pair of conductive wires extend from each jaw. The wires are bent so as to have an arcuate segment adjacent the jaws and they then extend rectilinearly through the length of lumen to a handle on the proximal end of the tube. Means for connecting the conductive wire pairs to an RF power source are provided at or near the handle.

A guide member is located in the lumen. The guide member has a first end consisting of a guide sleeve disposed proximate at the distal end of the lumen. Extending from the guide sleeve is a plurality of rectilinear tubular members. These tubular members receive the conductive wires extending from the forceps' jaws. The tubular members have a spaced apart parallel configuration so that the cutting blade rod can also extend through the lumen to provide longitudinal movement to the blade. The guide sleeve contains a slot for receiving the cutting blade and apertures through which the conductive wires can extend.

The bipolar coagulating forceps can be actuated independently of the cutting instrument in the first and second embodiment of the handle. Disposed on the proximal end of the tube is a scissors type handle which closes or opens the jaws by imparting movement to the guide sleeve at the distal end of the tubular member over the arcuate portions of the conductive wires extending from the coagulating forceps' jaws. As the guide sleeve moves towards the jaws, the arcuate portion is straightened, causing closure of the coagulating forceps. When the sleeve is returned, the spring properties of the arcuate wires cause the jaws to reopen.

In the first embodiment of the handle, a separate trigger mechanism is used to actuate the cutting instrument. A trigger lever is pivotally attached to the handle. A first end of the trigger lever is located within the handle and contains a socket. The blade actuating rod has a spherical proximal end dimensioned to fit into the socket. As the trigger lever is squeezed towards the handle's proximal end, the socket pivots towards the distal end of the handle, thereby extending the cutting instrument on the cutting instrument actuating rod's distal end. When the socket end of the trigger lever is pivoted towards the handle's proximal end, the cutting instrument is retracted.

In the second embodiment of the handle, the cutting instrument actuating rod is connected through a slit in the tubular member to a slidable exterior spool mechanism located on the proximal end of the tubular member, adjacent the handle. The exterior spool mechanism slides over the tubular member. Its range is limited by the length of the slit in the tubular member. Movement of the exterior spool towards the distal end extends the cutting instrument by the cutting instrument actuating rod. Movement of the exterior spool in the proximal direction retracts the cutting instrument.

In a third embodiment of the handle, the coagulating forceps and cutting instrument are reciprocated by a single scissors-like handle having a translating block and leaf spring assembly. The guide sleeve member is attached to a translating block and the cutting instrument actuating rod is attached to the end of a lever arm of the scissors-style handle. A leaf spring is connected to the translating block and the lever arm of the handle. Movement of the lever arm towards the proximal end will first cause movement of the translating block towards the distal end of the handle. This causes the guide sleeve to move toward the forceps, flattening the arcuate portion of the wires affixed to the forcep jaws. The forceps jaws are closed once the translating block reaches the distal end of the handle. Continued movement of the lever arm towards the handle's proximal end causes the cutting instrument to extend by way of the cutting instrument actuating rod. When the lever arm is returned to its original position, the cutting instrument retracts and then the forceps open.

DESCRIPTION OF THE DRAWINGS

The foregoing features and advantages of the invention will become apparent to those skilled in the art from the following detailed description of the present invention, in which like numerals in the several view refer to corresponding parts.

DESCRIPTION OF THE PREFERRED EMBODIMENT

Figure 1:
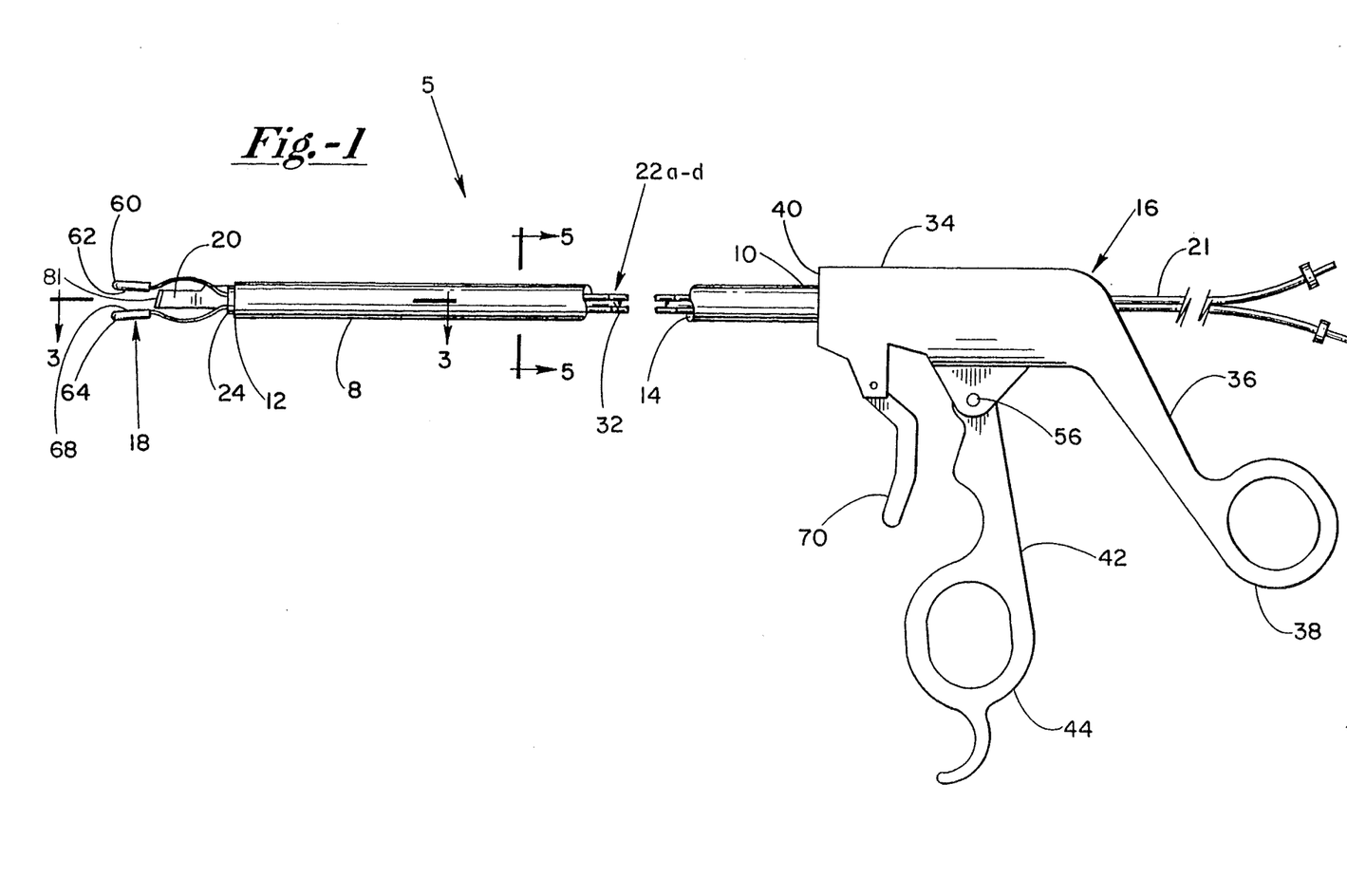
FIG. 1 is a partially cut away, side elevation of a bipolar surgical forceps in accordance with the present invention.

Referring first to FIG. 1, there is indicated generally by numeral 5 an electrosurgical instrument designed for use in percutaneous laparoscopic surgical procedures. The instrument comprises an elongated rigid tubular member 8 which may be formed from a variety of materials such as stainless steel. The outer tubular member 8 has a proximal end 10, a distal end 12 and a lumen 14 extending the entire length thereof. The outer tubular member 8 preferably has approximately a 8 mm lumen and is sized to be used within a trocar with a 10 mm inner diameter. A scissors type handle 16 is located at the proximal end of the outer tubular member 8. Coagulating forceps 18 and a cutting blade 20 extend out from the distal end of the outer tubular member 8. The instrument is connected through leads 21 to a source of RF power.

Figure 5:
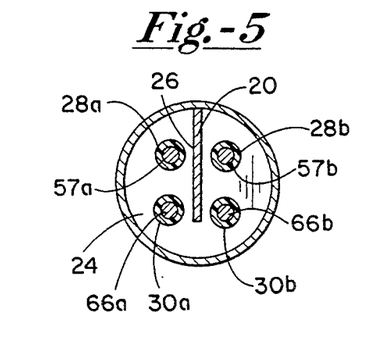
FIG. 5 is a cross sectional view taken along line 5—5 of FIG. 1.

Located in the lumen of the outer tubular member is a plurality of wire receiving tubular members 22a–22d, which extend the entire length of the tubular member 8 in spaced apart arrangement. Passing through these wire receiving tubular members 22a–22d are the conductor wires for the coagulating forceps 18. Also extending the length of the lumen of the outer tubular member 8 is a blade actuating rod 32 to which the blade 20 is affixed. The plurality of wire receiving tubular members 22a–22d are arranged in a spaced apart fashion so that the blade actuating rod 32 can readily reciprocate within the lumen without interference from the conductor wires. A wire guide sleeve 24 is located at the distal ends of the wire receiving tubular members 22a–22d and within the distal end of the lumen of the outer tubular member 8. As shown in FIG. 5, the wire guide sleeve 24 contains a slot 26 for receiving the cutting blade 20 therethrough and a plurality of wire receiving apertures 28a, 28b, 30a and 30b for receiving conductive wires therethrough.

Figure 2:
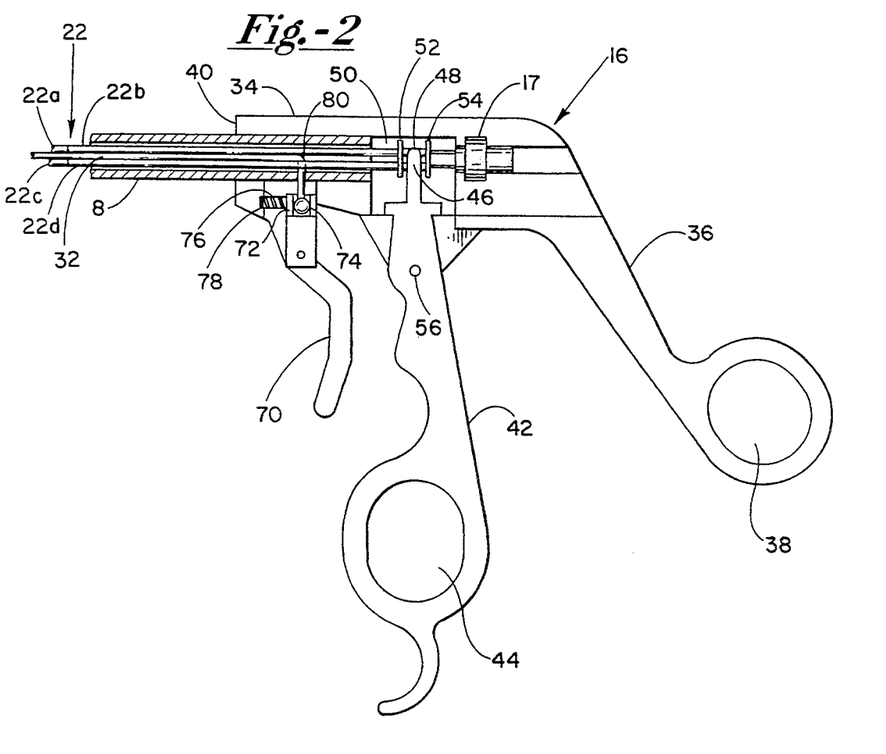
FIG. 2 is a side, sectioned view of the proximal end of the present invention.

The stationary handle 16 is made in two halves, only one of which is shown in FIG. 2. Each half has a longitudinally extending section 34 that terminates at the handle's distal end 40. The proximal end of the handle halves has a downward sloping arm 36 that terminates in an annular finger receiving opening 38. The proximal end of the outer tubular member 8 is frictionally fit into the distal end 40 of the handle. A moveable arm 42 is pivotally mounted on the handle at 56 and terminates in an annular finger receiving opening 44. The opposite end 46 of the moveable arm 42 is forked for engaging a cylindrical spool 48.

The cylindrical spool 48 is located in a cavity 50 of the longitudinally extending section 34 and has two opposing end flanges 52 and 54. The spool 48 is part of a slidable spool mechanism used for providing translational movement of the wire guide sleeve support 24 within the translationally stationary outer tubular member 8. The tubular members 22a–22d extend from the wire guide sleeve support 24 through the length of the lumen and frictionally fit onto the spool end flange 52.

The slidable spool mechanism further includes the pivotally mounted moveable arm 42 secured by a pivot pin 56 to the stationary handle 16. The moveable arm 42 has a forked end 46 which will engage the surfaces of the spool 48 between the two spool flanges 52 and 54, allowing movement of the spool 48 and the wire support sleeve 24 back and forth longitudinally. For example, the forked end 46 contacts the flange 52 of the spool when the moveable arm 42 is manipulated to close forceps 18 and contacts flange 54 when the moveable arm 42 is manipulated to open forceps 18.

Two pairs of conductive wire leads extend the entire length of the tubular member through the plurality of wire receiving tubular members 22a–22d. The first pair 57a and 57b are operatively connected to the first jaw 60 of the coagulating forceps 18 and to an electrical connector 17 located in the handle 16 for connecting the leads to a source of RF power. The wires 57a and 57b pass through the wire sleeve support 24 located at the wire receiving distal end of the inner tube, via apertures 28a and 28b, and through tubular members 22a and 22b. The wires 57a and 57b extend from the distal end of the tubular member 8 in spaced apart parallel arrangement for receiving the cutting blade 20, such as a scalpel blade therebetween. As earlier mentioned, the wires 57a and 57b also have an arcuate configuration just proximal of the flattened electrode surface 62 of the first jaw 60. The first jaw 60 has a slot, not shown, for receiving the cutting blade 20 therein.

Figure 3:
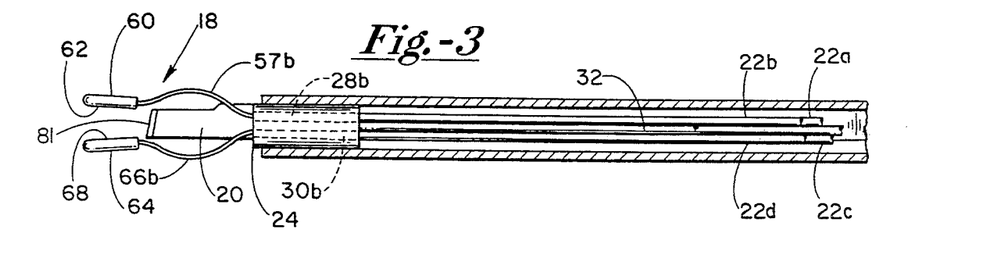
FIG. 3 is a partially sectioned side view of the distal end of the present invention taken along the line 3—3 in FIG. 1.
Figure 4:
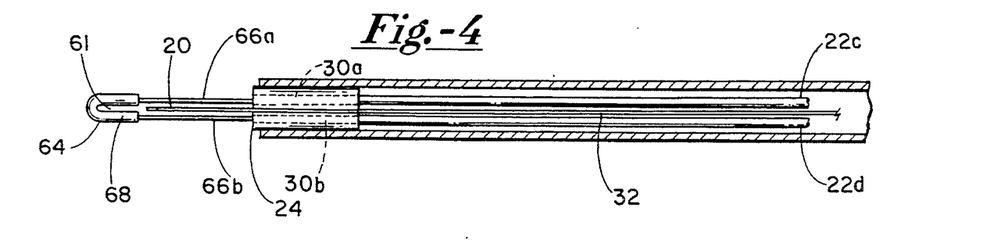
FIG. 4 is a sectional top view of the distal end of the present invention.

The second conductive wire lead pair 66a and 66b are operatively connected to the second jaw 64 of the coagulating forceps 18 and to the electrical connector 17 of the handle. As seen from FIGS. 3 and 4, the second conductive pair 66a and 66b extends from the distal end of the tubular member 8 in spaced apart, parallel arrangement to each other so that the cutting blade 20 can freely pass therebetween. The first conductive pair 57a and 57b has the identical spaced apart parallel arrangement as that shown in FIG. 4 for the second pair 66a and 66b. Like the first conductive pair, the second pair 66a and 66b extends in an arcuate fashion prior to joining to a flattened electrode surface 68 on jaw 64. The second jaw 64 has a slot 61 aligned with the slot on the first jaw 60 for receiving the blade 20 therein. The second pair of arcuate wires 66a and 66b is in spaced apart parallel arrangement to the first pair 57a and 57b such that the blade 20 can freely pass therebetween and into both slots.

The arcuate configuration of the conductive wires is necessary to accomplish the closing of the forceps 18 when the wire guide sleeve 24 is moved in the distal direction over the arcuate portion of the wires, thereby causing the arcuate portion to be squeezed together, closing the coagulating forceps' electrode surfaces 62 and 68 against one another or against tissue disposed therebetween. The wire support sleeve 24 is made to move longitudinally inside the outer tubular member 8 and over the leads by effecting longitudinal displacement of a slidable spool mechanism located inside the handle 16 via manipulation of the moveable arm 42 as will be explained later.

A cutting instrument actuating lever 70 is pivotally attached to the handle 16 near its distal end as shown in FIG. 1 and 2. The actuating lever 70, which extends into the longitudinal section 34 of the handle, contains a socket 72 for receiving the spherical end 74 of the cutting instrument actuating rod 32. A retaining spring 76 is located between the ball and socket arrangement and the wall 78 of the cavity 50.

The cutting instrument actuating rod 32 extends through the length of the tubular member 8 with its proximal end having an arcuate portion 80 extending into the spherical configuration 74 which is received by the socket 72 of the actuating lever 54. The distal end of the cutting instrument actuating rod 32 supports a conventional cutting blade 20 which can be crimped or otherwise affixed to the rod. The wire support member 24 contains a slot 26 through which the cutting blade 20 can move when reciprocated. The cutting blade has a sharpened cutting edge on its proximal edge 81.

Figure 8:
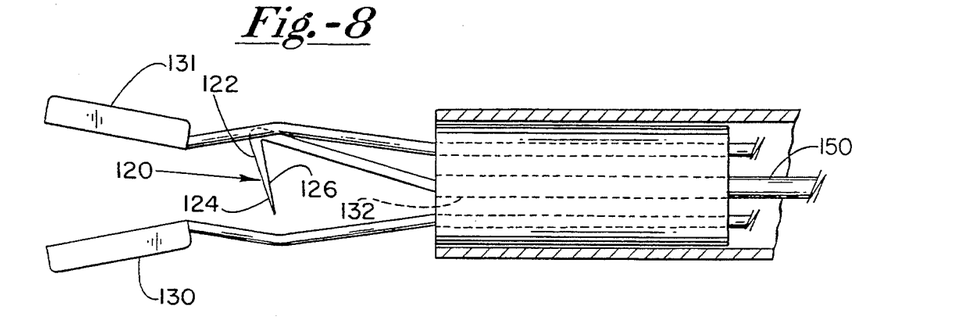
FIG. 8 is a cross sectional view of the second embodiment of the cutting instrument.

The second embodiment of the cutting instrument is a cutting wire 123 and shown in FIG. 8. The cutting wire has a hook shape with a downwardly depending leg 125. The leading and trailing edges 124 and 126 of the downwardly depending leg 125 are sharpened for cutting. The cutting wire 123 is a flexible springy wire that will permit it to flex upward if it is unable to cut through the tissue structure when it is advanced in the distal direction. However, it has enough resilience so that it will resume its original shape. The cutting wire 123 is affixed to the cutting instrument actuating rod in a conventional manner such as by soldering. The remaining features of the forceps are the same as the first embodiment.

Figure 9A:
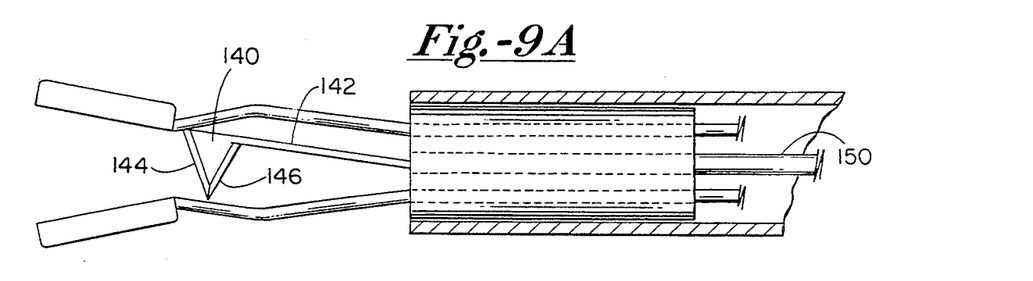
FIG. 9a and 9b are cross sectional views showing the third embodiment of the cutting instrument.
Figure 9B:
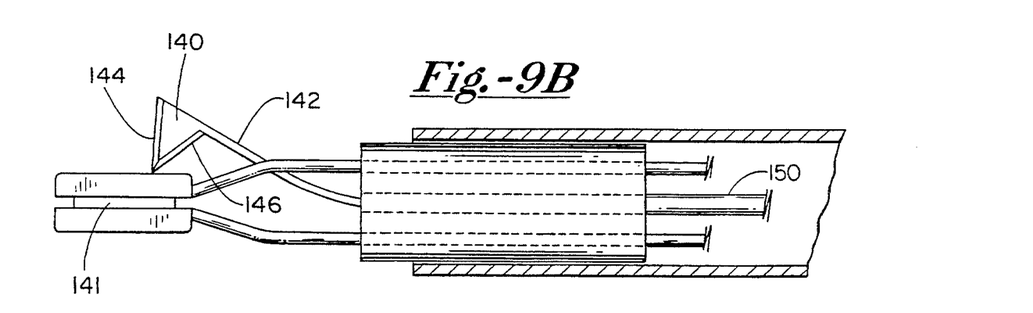

The third embodiment for the cutting instrument is shown in FIGS. 9a and 9b. This embodiment essentially has a triangular shaped or angled blade 140 at the proximal end. This blade can be made by notching out a trailing edge in a general rectangular scalpel blade or by affixing a triangular blade by way of an extending member 142 to the cutting instrument actuating rod. This blade has a sharpened cutting edge on its leading cutting edge 144 and on its trailing edge 146. The blade 140 is typically soldered to the blade actuating rod 150. The blade 140, like the cutting wire 123, is resilient enough to flex and ride up over obstructing tissue 141 so that when the blade 140 is pulled back cutting can take place on the return stroke and the blade 140 can return to its resting position. As shown in FIG. 9a, the blade 140 is in its resting position. FIG. 9b shows the blade 140 in its flex position for riding up over obstructing tissue 152. The remaining elements of the forceps are the same as the first embodiment.

The second and third embodiments of the cutting instruments are advantageous when the tissue to be cut meets an obstruction. The second and third cutting instruments are flexible so they will ride up over the tissue obstruction, such as shown by the flex position of FIG. 9b. When the blade is pulled back, cutting will then take place on the return stroke.

Figure 6:
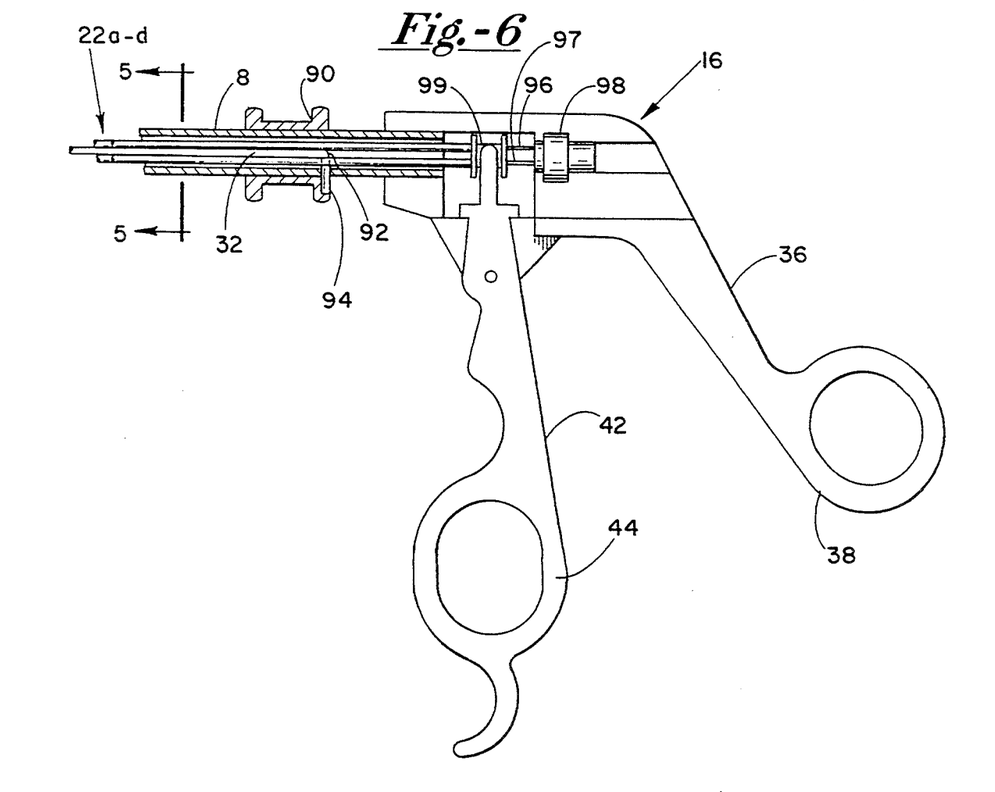
FIG. 6 is a cross sectional view showing a second embodiment of a handle mechanism for use in the present invention.

A second embodiment of the handle shown in FIG. 6 replaces the blade trigger 70 with an exterior spool 90, slidably located on the exterior of the outer tubular member 8. The cutting instrument rod 32 has an arcuate portion 92 which is joined at its end 94 to the exterior spool 90. The exterior spool 90 may be manually manipulated for longitudinal motion. The range of movement is limited by the end wall of a slot (not shown) located in the outer tubular member 8 through which the rod end 94 extends. The conductive leads 96 and 97 leads extend from the proximal end of an interior spool 99 to the electrical connector 98 to which elongated leads for the source of RF power connect. The interior spool 99 is part of an arrangement for actuating the forcep jaws identical to that in the first embodiment.

Figure 7A:
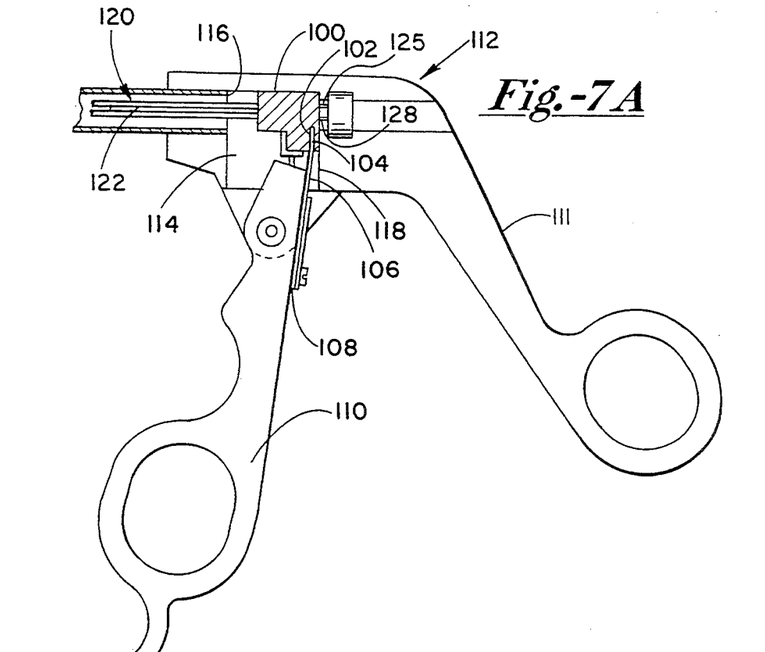
FIGS. 7a, 7b and 7c are cross sectional views helpful in understanding a third embodiment of the invention.
Figure 7B:
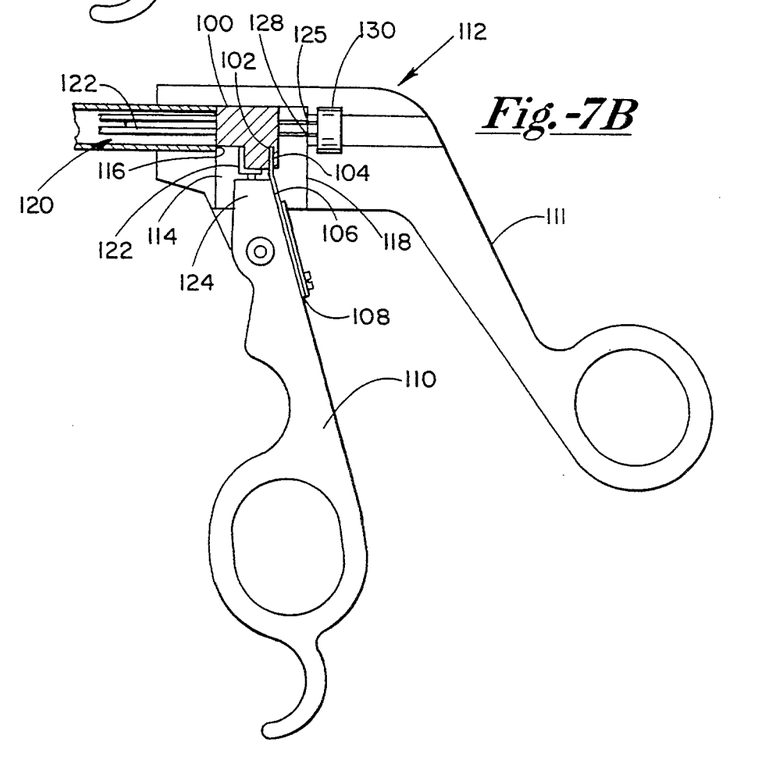
Figure 7C:
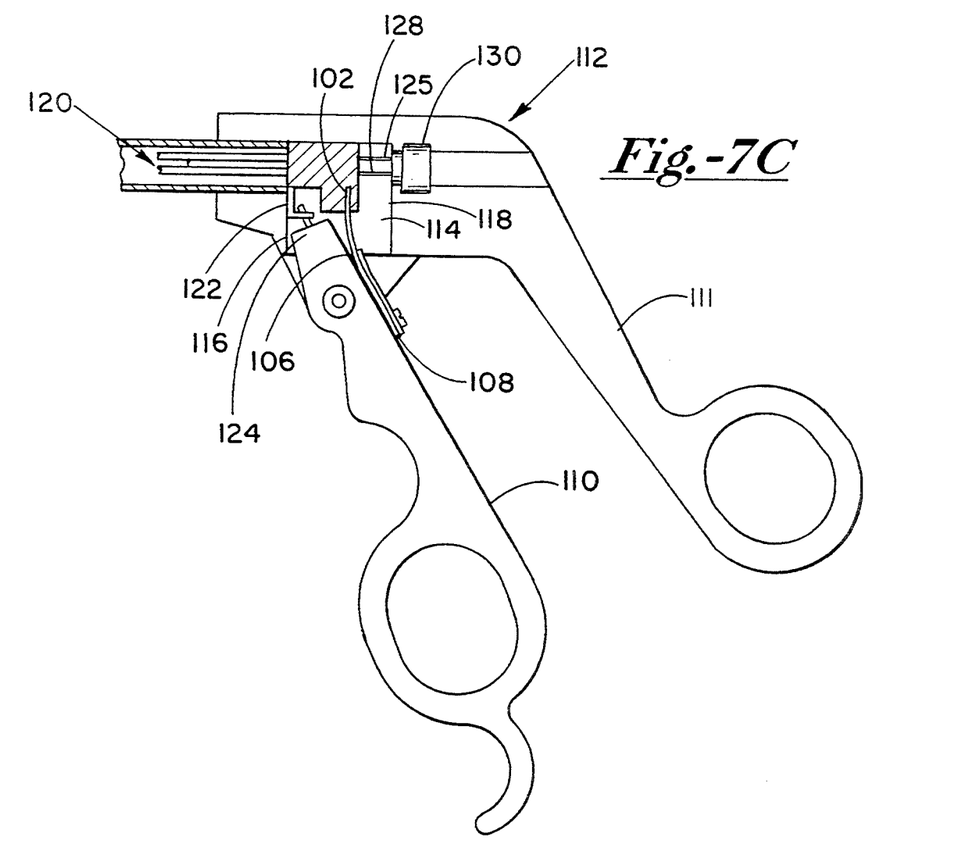

A third embodiment of the handle incorporates an actuating structure as illustrated in FIGS. 7a–7c for actuating the closing and opening of the electrode forceps 18 and actuation of the cutting blade 20 with operation of only the scissors handle mechanism. The structure includes a translating block 100 with a groove 102 for receiving a first end 104 of a leaf spring 106. The leaf spring 106 has a second end 108 fastened to a lever arm 110 of a handle 112. The translating block 100 is designed to move back and forth within a cavity 114, limited only by walls 116 and 118. The proximal ends of the plurality of wire receiving tubular members 120 are fixed to the translating block 100. The translating block also has a groove, not shown, for receiving the blade actuating rod 122. The blade actuating rod 122 is bent to be attached to the distal end 124 of the lever arm 110 of the scissors-style handle 112. Leads 125 and 126 extend from the proximal end 128 of the translating block 100 to the connector 130 to which the source of RF power attaches.

MODE OF OPERATION

The present invention is intended to be used in conjunction with the cannula, however, it is not limited to such use. In use, the instrument of FIG. 1 will have its tubular member 8 inserted through the lumen of a cannula extending through a puncture formed in the abdominal wall. The surgeon views a surgical site via a laparoscope and locates the tissue such as the cystic duct which links the gall bladder and the common bile duct. The bipolar coagulating forcep jaws 60 and 64 are positioned about the cystic duct at the location to be coagulated and cut. The surgeon then pulls the moveable handle arm 42 towards the stationary arm 36, causing the forked end 46 of arm 42, which engages the spool 48, to push the spool 48 towards the distal end of the handle 16. This movement causes the wire guide sleeve 24 to extend beyond the distal end of the tubular member 8. This motion facilitates the closing of the coagulating forceps' jaws 60 and 64 in that as the wire guide sleeve 24 reaches the arcuate portion of the wire conductors, it causes the arcuate portions of the wire conductors to be drawn together thereby closing the forceps' jaws 60 and 64 onto the tissue. As the tissue is clamped, RF power generated by the electrosurgical generator is applied which causes a current path to be developed between the electrode surfaces 62 and 68 on the jaws 60 and 64 to thereby heat and coagulate the tissue pinched between the two jaw electrodes.

The blade trigger 70 of the handle 16 is then pulled towards the moveable arm 42 of the handle 16. The socket 72 compresses the retaining spring 76 against wall 78 and the ball 74 allows the rod 1 32 to be reciprocated towards the distal end, causing the blade 20 to extend from the distal end of the tubular member 8, between the conductor pairs and within the blade receiving slots, one of which is shown as 61, formed in the electrodes. Once the tissue is cut, the blade is retracted by removing pressure from the blade trigger 70. The forceps' jaws 60 and 64 may be released by moving the pivotal arm 42 towards the blade trigger 70 of the handle 16 which retracts the guide sleeve, releasing the springy arcuate wire segments. If the cutting instrument meets an obstruction or difficult tissue to cut, the springy wire 120 of the second embodiment or the double edged blade 140 of the third embodiment will flex and ride up over the obstruction as shown in FIG. 9b. When the cutting wire or blade is retracted, cutting can occur on the back stroke. The cutting wire or blade can be moved back and forth until the tissue or obstruction is cut.

In the second embodiment shown in FIG. 6, the blade 20 is advanced or retracted by movement of the exterior spool 90. The blade 20 advances through the blade receiving slots of the forceps 18 as the exterior spool 90 is moved towards the distal end of the device. The slot (not shown) limits the range of travel. The blade 20 retracts from the blade receiving slots and into the wire sleeve support 24 as the exterior spool 90 is manually moved towards the handle 16.

In the third handle embodiment, the coagulating forceps close when the lever arm 110 is moved towards the stationary arm 111 of the handle 112, causing the translating block 100 to move, via the leaf spring 106, towards the distal end of the handle 16 within the cavity 114. The forceps' jaws are closed when the translating block 100 contacts the wall 116 of the cavity 114 as seen in FIG. 7b. Additional movement of the pivotal arm 110 towards the stationary arm 111 causes the blade 20 to be extended into the blade receiving slots since the rod 122 is fixed to the tip of the pivotal arm 110 inside the cavity 114.

FIGS. 7a–7c show the inter-relationship of the leaf spring and translating block as the forceps are closed and the blade is extended. FIG. 7a shows the position when the blade is retracted and the jaws are open. In FIG. 7b, the translating block abuts cavity wall 116 such that the jaws are closed and the blade 20 is only partially extended. The blade 20 becomes fully extended with the jaws are fully closed when continued movement of the arm 110 takes place against the force of the leaf spring 106. As show in these three figures, the leaf spring 106 allows the lever arm 110 to pivot an additional amount after the translating block 100 abuts the cavity wall 116 so to fully extend the blade 20.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A bipolar electrosurgical device for coagulating and cutting tissue, said device comprising;
   (a) an elongated tubular member having a proximal end, a distal end and a lumen extending therethrough;
   (b) a first moveable forceps jaw and a second moveable forceps jaw extending from said distal end of said tubular member;
   (c) a means for opening and closing said first and second moveable forceps jaws relative to one another;
   (d) a first electrode on said first moveable forceps jaw and a second electrode on said second moveable forceps jaw;
   (e) means for applying a RF voltage across said first and second electrodes for coagulating tissue contained between said first and second moveable forceps jaws;
   (f) a cutting instrument extending from said distal end of said tubular member; and
   (g) a reciprocating means for advancing and retracting said cutting instrument through said tissue when contained between said jaws.

2. A device of claim 1 wherein said means for opening and closing said first and second moveable forceps jaws includes at least one first arcuate wire member extending proximal of said first moveable forceps jaws and at least one second arcuate wire member extending proximal of said second moveable forceps jaws and further including a moveable guide sleeve means for selectively engaging and deforming said at least one first and second arcuate wire members.

3. A device of claim 2 wherein said means for opening and closing said forceps jaws includes a handle at said proximal end of said tubular member, said handle having a stationary element coupled to said proximal end of said tubular member and a moveable element coupled to said stationary element.

4. A device of claim 3 and further including a spool member wherein said moveable element is pivotally joined to said stationary element with said moveable element having a first end coupled to said spool member and a second end of said moveable element configured for manual manipulation.

5. A device of claim 3 wherein said handle further includes a trigger member operatively connected to said reciprocating means for advancing and retracting said cutting instrument.

6. A device of claim 3 further including an exterior spool slidingly surrounding said tubular member and operatively connected to said reciprocating means for advancing and retracting said cutting instrument.

7. The device of claim 3 and further including a translating block operatively Joined to a proximal end of the moveable guide sleeve means and coupled to the moveable element for selectively engaging and deforming said at least one first and second arcuate wire members when the movable element is actuated; and a movable rod affixed to said cutting instrument, the movable rod also being coupled to said movable element.

8. A device of claim 1 wherein said cutting instrument is a scalpel blade having a sharpened cutting leading edge.

9. A device of claim 1 wherein said cutting instrument is flexible and has a leading cutting edge and a trailing cutting edge.

10. A device of claim 1 wherein said cutting instrument is a springy wire having a leading edge and a trailing edge sharpened for cutting.

11. A device of claim 1 wherein said cutting instrument is a flexible scalpel blade having a leading edge and a trailing edge sharpened for cutting.

12. A bipolar electrosurgical device for coagulating and cutting tissue, said device comprising:
   (a) an elongated tubular member having a proximal end, a distal end and a lumen extending therethrough;
   (b) a tissue cutting instrument extending from said distal end of said elongated tubular member;
   (c) a moveable rod connected to said cutting instrument, said movable rod extending through said lumen;
   (d) first and second arcuate wire segments extending from the distal end of the elongated tubular member;
   (e) a forceps having a first moveable jaw extending from said first arcuate wire segment and a second moveable jaw extending from said second arcuate wire segment, said first moveable jaw having a first electrode surface and said second moveable jaw having a second electrode surface, said first electrode surface and said second electrode surface adapted to be operatively connected to a source of RF voltage;
   (f) a guide sleeve member disposed within said lumen of said elongated tubular member for selectively engaging said first and second arcuate wire segments when said guide sleeve member is translated for closing said first and second moveable jaws; and
   (g) a handle member affixed to said proximal end of said tubular member, said handle member including means for imparting translational reciprocal motion to said guide sleeve member and said moveable rod.

13. The device of claim 12 wherein said first electrode surface has a first slot for receiving said cutting instrument and said second electrode surface has a second slot for receiving said cutting instrument, said second slot being aligned parallel with said first slot in different planes.

14. The device of claim 12 wherein said guide sleeve member includes a cutting instrument receiving slot for receiving said cutting instrument therethrough and at least one wire receiving aperture for receiving one of said first and second arcuate wire segments therethrough.

15. The device of claim 12 wherein said handle member comprises a stationary element coupled to said proximal end of said tubular member and a moveable element pivotally jointed to said stationary element with said moveable element having a first end coupled to said guide sleeve member and a second end of said moveable element configured for manual manipulation.

16. The device of claim 15 wherein said handle member further includes a spool member affixed to said proximal end of said guide sleeve member, with said first end of said moveable element being forked for engaging said spool member.

17. The device of claim 15 wherein said means for imparting translational reciprocal motion to said guide member includes a translating block operatively joined to said guide sleeve member and a biasing means connecting said translating block and said moveable element.

18. The device of claim 12 wherein said means for imparting translational reciprocal motion to said guide sleeve member and said movable rod includes a trigger member operatively coupled to said moveable rod for imparting translational movement to said cutting instrument.

19. The device of claim 12 wherein said means for imparting translational reciprocal motion to said guide sleeve member and said moveable rod includes an exterior spool operatively connected to said moveable rod.

20. A device of claim 12 wherein said cutting instrument is a scalpel blade having a sharpened cutting leading edge.

21. A device of claim 12 wherein said cutting instrument is flexible and has a leading cutting edge and a trailing cutting edge.

22. A device of claim 12 wherein said cutting instrument is a springy wire having a sharpened leading edge and a sharpened trailing edge.

23. A devise of claim 12 wherein said cutting instrument is a flexible scalpel blade having a sharpened leading edge and a trailing edge.

* * * * *

UNITED STATES PATENT AND TRADEMARK OFFICE
CERTIFICATE OF CORRECTION

PATENT NO. : 5,445,638
DATED : August 29, 1995
INVENTOR(S) : Mark A. Rydell and Joseph A. O'Brien It is certified that error appears in the above-indentified patent and that said Letters Patent is hereby corrected as shown below:

Column 10, line 12, change "Joined" to --joined--;

Column 11, line 23, before "member" insert --sleeve--; and

Signed and Sealed this

Second Day of January, 1996

*Attest:*

BRUCE LEHMAN

*Attesting Officer*  *Commissioner of Patents and Trademarks*

REEXAMINATION CERTIFICATE (3510th)

United States Patent [19]
Rydell et al.

[11] B1 5,445,638
[45] Certificate Issued May 5, 1998

[54] BIPOLAR COAGULATION AND CUTTING FORCEPS

[75] Inventors: Mark A. Rydell, Golden Valley; Joseph A. O'Brien, Fridley, both of Minn.

[73] Assignee: Everest Medical Corporation, Minneapolis, Minn.

Reexamination Request:
No. 90/004,184, Mar. 14, 1996

Reexamination Certificate for:
Patent No.: 5,445,638
Issued: Aug. 29, 1995
Appl. No.: 92,558
Filed: Jul. 16, 1993

Certificate of Correction issued Jan. 2, 1996.

Related U.S. Application Data

[63] Continuation-in-part of Ser. No. 28,897, Mar. 8, 1993, abandoned.
[51] Int. Cl.$^6$ ............................................. A61B 17/39
[52] U.S. Cl. ................................. 606/51; 606/171
[58] Field of Search ..................... 606/45, 46, 48–52, 606/171

[56] References Cited

U.S. PATENT DOCUMENTS

| | | |
|---|---|---|
| 2,068,721 | 1/1937 | Wappler et al. . |
| 3,920,021 | 11/1975 | Hiltebrandt . |
| 4,003,380 | 1/1977 | Wien . |
| 4,005,714 | 2/1977 | Hiltebrandt . |
| 4,452,546 | 6/1984 | Hiltebrandt et al. . |
| 4,461,305 | 7/1984 | Cibley . |
| 4,532,924 | 8/1985 | Auth et al. . |
| 4,655,216 | 4/1987 | Tischer ............................ 606/51 |
| 4,977,900 | 12/1990 | Fehling et al. . |
| 5,009,661 | 4/1991 | Michelson . |
| 5,078,717 | 1/1992 | Parins et al. . |
| 5,258,006 | 11/1993 | Rydell et al. ..................... 606/51 |

FOREIGN PATENT DOCUMENTS

| | | |
|---|---|---|
| 0517244 | 12/1992 | European Pat. Off. . |
| 0518230 | 12/1992 | European Pat. Off. . |
| 2355521 | 1/1978 | France ........................... 606/52 |
| 280911 | 3/1979 | Germany . |
| 3709067 | 9/1988 | Germany . |
| 649420 | 3/1979 | U.S.S.R. . |

*Primary Examiner*—Lee S. Cohen

[57] ABSTRACT

A bipolar electrosurgical device for coagulating and cutting tissue has an elongated tubular member from which a bipolar tissue cutting forceps and cutting instrument extends at the distal end. The cutting instrument is connected to a moveable rod extending through the lumen of the tubular member. A first and second conductor pair extend in spaced apart parallel arrangement to allow the cutting instrument and its moveable rod to extend therebetween. The first and second conductor pairs are operatively connected to the forceps jaws. A moveable guide member is disposed within the lumen of the elongated tubular member and has means for selectively engaging the first and second conductor pairs for closing and opening jaws of the forceps. The forceps jaws have a slot for receiving the cutting instrument therebetween. A handle member is fixed to the proximal end of the first tubular member. The handle member includes means for imparting translational longitudinal reciprocal motion to the guide member and the cutting instrument for a coagulating and cutting procedure. The cutting instrument may have one cutting edge on the leading edge or a cutting edge on both the leading and trailing edge.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, line 55–column 5, line 2:

Referring first to FIG. 1, there is indicated generally by numeral 5 an electrosurgical instrument designed for use in percutaneous laparoscopic surgical procedures. The instrument comprises an elongated rigid tubular member 8 which may be formed from a variety of materials such as stainless steel. The outer tubular member 8 has a proximal end 10, a distal end 12 and a lumen 14 extending the entire length thereof. The outer tubular member 8 preferably has approximately a 8 mm lumen and is sized to be used within a trocar with a 10 mm inner diameter. A scissors type handle 16 is located at the proximal end of the outer tubular member 8. Coagulating forceps 18 and [a] *an electrically passive, generally planar* cutting blade 20 extend out from the distal end of the outer tubular member 8. The instrument is connected through leads 21 to a source of RF power.

Column 5, line 55–column 6, line 4:

Two pairs of conductive wire leads extend the entire length of the tubular member through the plurality of wire receiving tubular members 22a–22d. The first pair 57a and 57b are operatively connected to the first jaw 60 of the coagulating forceps 18 and to an electrical connector 17 located in the handle 16 for connecting the leads to a source of RF power. The wires 57a and 57b pass through the wire sleeve support 24 located at the wire receiving distal end of the inner tube, via apertures 28a and 28b, and through tubular members 22a and 22b. The wires 57a and 57b extend from the distal end of the tubular member 8 in spaced apart parallel arrangement for receiving the cutting blade 20, such as a *generally planar* scalpel blade therebetween. As earlier mentioned, the wires 57a and 57b also have an arcuate configuration just proximal of the flattened electrode surface 62 of the first jaw 60. The first jaw 60 has a slot, not shown, for receiving the cutting blade 20 therein.

Column 7, lines 3–21:

The third embodiment for the cutting instrument is shown in FIGS. 9a and 9b. This embodiment essentially has a *generally planar, electrically passive* triangular shaped or angled blade 140 at the proximal end. This blade can be made by notching out a trailing edge in a general rectangular scalpel blade or by affixing a triangular blade by way of an extending member 142 to the cutting instrument actuating rod. This blade has a sharpened cutting edge on its leading cutting edge 144 and on its trailing edge 146. The blade 140 is typically soldered to the blade actuating rod 150. The blade 140, like the cutting wire 123, is resilient enough to flex and ride up over obstructing tissue 141 so that when the blade 140 is pulled back cutting can take place on the return stroke and the blade 140 can return to its resting position. As shown in FIG. 9a, the blade 140 is in its resting position. FIG. 9b shows the blade 140 in its flex position for riding up over obstructing tissue 152. The remaining elements of the forceps are the same as the first embodiment.

AS A RESULT OF REEXAMINATION, IT HAS BEEN DETERMINED THAT:

Claims 10 and 22 are cancelled.

Claims 1, 5–9, 11–14, 18, 20, 21 and 23 are determined to be patentable as amended.

Claims 2–4, 15–17 and 19, dependent on an amended claim, are determined to be patentable.

1. A bipolar electrosurgical device for coagulating and cutting tissue, said device comprising;
   (a) an elongated tubular member having a proximal end, a distal end and a lumen extending therethrough;
   (b) a first moveable forceps jaw and a second moveable forceps jaw extending from said distal end of said tubular member;
   (c) a means for opening and closing said first and second moveable forceps jaws relative to one another;
   (d) a first electrode on said first moveable forceps jaw and a second electrode on said second moveable forceps jaw;
   (e) means for applying a RF voltage across said first and second electrodes for coagulating tissue contained between said first and second moveable forceps jaws;
   (f) [a] *an electrically passive, generally planar* cutting [instrument] *blade with a sharpened edge* extending from said distal end of said tubular member; and
   (g) a reciprocating means for advancing and retracting *the sharpened edge of* said cutting [instrument] *blade longitudinally* through said tissue when contained between said jaws.

5. A device of claim 3 wherein said handle further includes a trigger member operatively connected to said reciprocating means for advancing and retracting said cutting [instrument] *blade*.

6. A device of claim 3 further including an exterior spool slidingly surrounding said tubular member and operatively connected to said reciprocating means for advancing and retracting said cutting [instrument] *blade*.

7. The device of claim 3 further including a translating block operatively joined to a proximal end of the moveable guide sleeve means and coupled to the moveable element for selectively engaging and deforming said at least one first and second arcuate wire members when the movable element is actuated; and a movable rod affixed to said cutting [instrument] *blade*, the movable rod also being coupled to said movable element.

8. A device of claim 1 wherein said cutting [instrument] *blade* is a scalpel blade having a sharpened cutting leading edge.

9. A device of claim 1 wherein said cutting [instrument] *blade* is flexible and has a leading cutting edge and a trailing cutting edge.

11. A device of claim 1 wherein said cutting [instrument] *blade* is a flexible scalpel blade having a leading edge and a trailing edge sharpened for cutting.

12. A bipolar electrosurgical device for coagulating and cutting tissue, said device comprising;
   (a) an elongated tubular member having a proximal end, a distal end and a lumen extending therethrough;
   (b) [a] *an electrically passive, generally planar* tissue cutting [instrument] *blade having a sharpened edge and* extending from said distal end of said elongated tubular member;
   (c) a moveable rod connected to said cutting [instrument] *blade*, said movable rod extending through said lumen;

(d) first and second arcuate wire segments extending from the distal end of the elongated tubular member;

(e) a forceps having a first moveable jaw extending from said first arcuate wire segment and a second moveable jaw extending from said second arcuate wire segment, said first moveable jaw having a first electrode surface and said second moveable jaw having a second electrode surface, said first electrode surface and said second electrode surface adapted to be operatively connected to a source of a RF voltage;

(f) a guide sleeve member disposed within said lumen of said elongated tubular member for selectively engaging said first and second arcuate wire segments when said guide sleeve member is translated for closing said first and second moveable jaws; and (g) a handle member affixed to said proximal end of said tubular member, said handle member including means for imparting translational reciprocal motion to said guide sleeve member and said moveable rod.

13. The device of claim 12 wherein said first electrode surface has a first slot for receiving said cutting [instrument] *blade* and said second electrode surface has a second slot for receiving said cutting [instrument] *blade*, said second slot being aligned parallel with said first slot in different planes.

14. The device of claim 12 wherein said guide sleeve member includes a cutting [instrument] *blade* receiving slot for receiving said cutting [instrument] *blade* therethrough and at least one wire receiving apparatus for receiving one of said first and second arcuate wire segments therethrough.

18. The device of claim 12 wherein said means for imparting translational reciprocal motion to said guide sleeve member and said moveable rod includes a trigger member operatively coupled to said moveable rod for imparting translation movement to said cutting [instrument] *blade*.

20. A device of claim 12 wherein said cutting [instrument] *blade* is a scalpel blade having a sharpened cutting leading edge.

21. A device of claim 12 wherein said cutting [instrument] *blade* is flexible and has a leading cutting edge and trailing cutting edge.

23. A device of claim 12 wherein said cutting [instrument] *blade* is a flexible scalpel blade having a sharpened leading edge and a trailing edge.

* * * * *